United States Patent [19]

Dutra et al.

[11] 4,395,374

[45] Jul. 26, 1983

[54] ALKYL N-ARYLSULFENYL-N-DIARYLOXY-PHOS-PHINYLMETHYLGLYCINATES

[75] Inventors: Gerard A. Dutra, Ladue, Mo.; James A. Sikorski, West Lafayette, Ind.

[73] Assignee: Monsanto Company, St. Louis, Mo.

[21] Appl. No.: 222,213

[22] Filed: Jan. 2, 1981

[51] Int. Cl.$^3$ .......................... C07F 9/40; A01N 57/22
[52] U.S. Cl. ........................ 260/941; 71/87; 260/940; 260/968; 549/221
[58] Field of Search ................. 260/941, 940; 549/221

[56] References Cited

U.S. PATENT DOCUMENTS

| | | | |
|---|---|---|---|
| 4,067,719 | 1/1978 | Dutra | 71/87 |
| 4,120,689 | 10/1978 | Dutra | 260/944 |
| 4,252,554 | 2/1981 | Dutra et al. | 71/87 |

OTHER PUBLICATIONS

Hopkins, et al. "J. Org. Chem.", vol. 43, No. 6, (1978) pp. 1208–1217.

*Primary Examiner*—Anton H. Sutto
*Attorney, Agent, or Firm*—Donald W. Peterson; Gordon F. Sieckmann

[57] ABSTRACT

This disclosure relates to arylsulfenyl derivatives of benzyl and aryl esters of N-phosphonomethylglycines. This disclosure further relates to herbicidal compositions containing arylsulfenyl derivatives of benzyl and aryl esters of N-phosphonomethylglycines, to the use thereof, and to herbicidal methods employing such compounds and compositions.

12 Claims, No Drawings

ALKYL N-ARYLSULFENYL-N-DIARYLOXY-PHOSPHINYLMETHYLGLYCINATES

This invention relates to arylsulfenyl derivatives of benzyl and aryl esters of N-phosphonomethylglycines. This invention further relates to herbicidal compositions containing arylsulfenyl derivatives of benzyl and aryl esters of N-phosphonomethylglycines to the use thereof and to herbicidal methods employing such compounds to plant growth regulator compositions, and to the use thereof.

U.S. Pat. No. 4,120,689 issued to Gerard A. Dutra on Oct. 17, 1978 describes alkyl-[di(benzyl) or di(aryl)]esters of N-phosphonomethylglycine which are produced by the reaction of a dibenzyl or diaryl phosphite with an N-methylene alkyl glycinate trimer. These esters and the hydrolysis products thereof containing at least one benzyloxy or aryloxy group bonded to phosphorus are compounds disclosed as having the formula

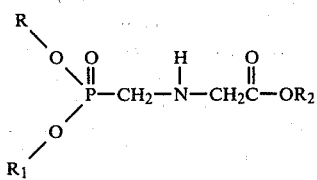

wherein R is a member of the group consisting of phenyl, benzyl, naphthyl, biphenylyl, and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro or halo; $R_1$ is hydrogen or an R group, and $R_2$ is a lower alkyl group or hydrogen, and the strong acid salts of the compounds wherein neither $R_1$ or $R_2$ is H. The aforementioned compounds are disclosed as useful as post-emergent herbicides.

The compounds of the present invention are represented by the formula

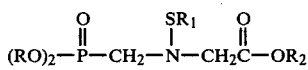

wherein R is phenyl, naphthyl, biphenylyl, benzyl, or naphthyl, biphenylyl, benzyl or phenyl substituted with from one to three substituents independently selected from the group consisting of hydrogen, lower alkyl, lower alkoxy, lower alkylthio, trifluoromethyl, alkoxycarbonyl, methylenedioxy, cyano, nitro and halogen; $R_1$ is naphthyl, phenyl or phenyl substituted with from one to three substituents independently selected from the group consisting of hydrogen, lower alkyl, lower alkoxy, halogen, trifluoromethyl and nitro; $R_2$ is selected from the group consisting of lower alkyl and lower aralkyl.

It is preferred that R is phenyl or substituted phenyl. Also, it is preferred that the substituted phenyl groups represented by R and $R_1$ contain one or two substituents.

Illustrative of the substituted phenyl groups which R and $R_1$ represent are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl, and the like, and di- and tri-substituted phenyl groups wherein the substituents are the same or different and are located in the 2, 3, 4, 5 or 6 positions of the phenyl ring, for example, dichlorophenyl, dinitrophenyl, dimethylphenyl, methylchlorophenyl, ethylfluorophenyl, dibutoxyphenyl, butylnitrophenyl, methylthiochlorophenyl, di(ethylthio)phenyl, trimethylphenyl, trichlorophenyl, tributylphenyl, ethyldichlorophenyl, 4-chloro-3-methylphenyl and the like.

Groups representative of the substituted biphenylyl groups represented by R include methylbiphenylyl, nitrobiphenylyl, bromobiphenylyl, dimethylbiphenylyl, difluorobiphenylyl, trimethylbiphenylyl and the like.

As employed throughout the claims and description, the term "lower alkyl" designates alkyl radicals which have up to four carbon atoms in a straight or branched chain, such as methyl, ethyl, propyl, isopropyl, butyl, isobutyl, sec-butyl and t-butyl.

As employed throughout the claims and description, the term "lower alkoxy" designates alkoxy radicals which have 1 to 4 carbon atoms in a straight or branched chain such as methoxy, ethoxy, propoxy, isopropoxy, butoxy, isobutoxy, sec-butoxy and t-butoxy.

Illustrative lower aralkyl include benzyl and phenylethyl.

In accordance with the present invention, the benzyl and aryl esters of N-phosphonomethylglycines of formula (I) are prepared by reacting a compound of the formula

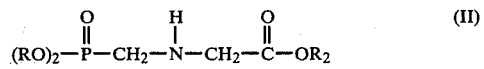

wherein R and $R_2$ are defined as above, in an aprotic solvent, with a compound of the formula

wherein $R_1$ is as defined above, in the presence of a hydrogen chloride acceptor.

Typical compounds of formula (III) are aryl sulfenyl chlorides. The method employed for the preparation of aryl sulfenyl chlorides of formula (III) is based on the quantitative reaction of aryl thiols with N-chloro-succinimide to give a reagent solution which comprises arylsulfenyl chloride as well as the "inert" co-product succinimide. The reagent solution is stirred at room temperature of about 25° C. from about 1 to 3 hours, cooled in an ice bath, and a solvent such as carbon tetrachloride is added to precipitate the succinimide. The resulting mixture is then filtered under nitrogen and transferred to the glycinate, amine and toluene solution. Typically aryl sulfenyl chloride is prepared in situ employing the aforedescribed methods are particularly described in "Chlorosulfenylation-Dehydrochlorination Reactions. New and Improved Methodology for the Synthesis of Unsaturated Aryl Sulfides and Aryl Sulfones" by Hopkins, Paul B. and Fuchs, Philip L., Department of Chemistry, Purdue University, West Lafayette, Ind. 47907, J. Org. Chem., Vol. 43, No. 6, (1978) pages 1208–1217, the teachings of which are incorporated herein in their entirety by reference.

It has been found that the temperature employed for the reaction of aryl sulfenyl chloride with compounds of formula (II) is in the range from about 0° to about 100° C. For ease of reaction and recovery of product, it is preferred to conduct the reaction in the range from about 10° to about 30° C.

In preparing the compounds of formula (I), the molar ratio of reactants is not narrowly critical. For best results, however, for each mole of a compound of formula (II), one should employ about one mole of an aryl sulfenyl chloride of formula (III) to produce one mole of a compound of formula (I). However, it is preferred to employ an excess of an aryl sulfenyl chloride of formula (III) for ease of reaction and maximum yield of product.

The hydrogen chloride acceptor is preferably employed in excess of stoichiometric requirements to insure completeness of reaction.

The hydrogen chloride acceptor is an amine, preferably a tertiary amine, which is inert to reactants employed and products formed. Examples of suitable tertiary amine hydrogen chloride acceptors include trimethylamine, triethylamine, tributylamine, trihexylamine, 1,5-diazabicyclo-[5.4.0]-undec-5-ene, pyridine, quinoline and the like. Triethylamine is the preferred hydrogen chloride acceptor.

Due to the highly reactive nature of the various reactants and intermediates, the process of the present invention should be conducted in an aprotic solvent under essentially anhydrous conditions. Illustrative aprotic solvents employable in the process of this invention include benzene, toluene, tetrahydrofuran, cyclohexane, methylcyclohexane, hexane, octane, dioxane, ethyl ether and the like, although toluene is the preferred aprotic solvent.

While the processes of this invention can be conducted at atmospheric, sub-atmospheric or super-atmospheric pressure, for convenience and economy it is generally preferred to conduct these processes at atmospheric pressure.

The following illustrative, non-limiting examples will serve to further demonstrate the manner in which specific compounds within the scope of this invention can be prepared and used. In the examples, all parts are parts by weight unless otherwise expressly stated.

EXAMPLE 1

A benzene solution (250 ml) of commercially available 2,4 dinitrophenylsulfenyl chloride (12.8 g, 0.053 mole) was added dropwise to a benzene solution (250 ml) of ethyl N-[(bis-4-methoxyphenoxy)phosphinylmethyl]glycinate (21.5 g, 0.050 mole) and triethylamine (20.2 g, 0.20 mole) at a temperature of 25° C. to form a reaction mixture. This reaction mixture was stirred for 6 days and then filtered to remove solids. The mother liquor was concentrated to a dark oil which was then titurated with ethyl ether and decanted. The ethyl ether solution was then concentrated to give a dark oil (A).

A first portion of dark oil (A) was purified by column chromatography over silica gel eluting with cyclohexane/ethyl acetate to give ethyl N-(2,4-dinitrophenylthio)-N-[(bis-4-methoxyphenoxy) phosphinylmethyl]glycinate (3.5 g, 29% yield) as a hydrated yellow oil, $n_D^{25}$ 1.5898.

Anal. Calculated for $C_{25}H_{26}N_3O_{11}PS \cdot H_2O$: C 48.00; H 4.51; N 6.72. Found: C 47.75; H 4.36; N 6.30.

EXAMPLE 2

The remaining portion of oil (A) prepared in Example 1 was stirred in ether/Benzene, allowed to stand 7 days and the solids which formed were collected by filtration. These solids were stirred in $CHCl_3$, filtered to remove insolubles, concentrated to an oil, stirred in benzene, filtered to remove insolubles. Yellow crystals formed in this benzene solution in a few days upon standing. The yellow solids were collected by filtration and washed with ethyl acetate to give ethyl N-(2,4-dinitrophenylthio)-N-[(bis-4-methoxyphenoxy)phosphinylmethyl]glycinate yield as a yellow solid, m.p. 124°–125° C. A proton NMR indicated that the structure of these yellow solids was identical to the structure of the hydrated oil of Example 1.

Anal. Calculated for $C_{25}H_{26}N_3O_{11}PS$: C49.43; H 4.31; N 6.92. Found: C 49.56; H 4.22; N 6.92.

EXAMPLE 3

2,4-Dinitrophenylsulfenyl chloride (5 grams, 0.021 moles) in benzene was added to a solution comprising ethyl N-[(bis-4-methoxyphenoxy)phosphinylmethyl]glycinate (8 grams, 0.0195 moles) and triethylamine (2.3 grams, 0.023 moles) in 100 ml. of toluene. The resulting composition turned a brown color and was stirred for 13 days at 25° C. whereby a yellow solid was formed. This solid was removed by filtration. The resulting filtrate was concentrated to a brown oil. This oil was extracted with diethyl ether. $^{31}P$ NMR spectral analysis of the ether extracts indicated a mixture of the desired sulfenamide and unreacted starting material. This crude product was adsorbed onto silica gel and purified by medium pressure liquid chromatography eluting with 60:40 cyclohexane/ethyl acetate to give ethyl N-(2,4 dinitrophenylthio)-N-[(bis-4-methoxyphenoxy)phosphinylmethyl]glycinate as a yellow solid (1.3 grams, 11% yield) m.p. 112°–116° C.

Anal. Calculated for $C_{25}N_{26}N_3O_{11}PS$: C, 49.43; H, 4.31; N, 6.92; S, 5.28. Found: C, 49.55; H, 4,36; N, 6.89; S, 5.26.

In the following Examples 4–11, the aryl sulfenyl chloride employed as a reactant was generated in situ according to the aforedescribed methods disclosed in J. Org. Chem. supra.

EXAMPLE 4

4-Methylphenylsulfenyl chloride (3.67 grams, 0.023 moles) previously generated in situ was added to a solution of methyl N-[(bis-4-methoxyphenoxy) phosphinylmethyl]glycinate (9.2 grams, 0.023 moles) and triethylamine (2.3 grams, 0.023 moles) in 100 ml. of toluene to form a reaction mixture. The mixture was stirred for 16 hours at a temperature of 25° C., filtered and concentrated to give a dark orange oil. Purification of the dark orange oil by medium pressure chromatography eluting with 50:50 cyclohexane/ethyl acetate gave Methyl N-(4-methyl-phenylthio)-N-[(bis-4-methoxyphenoxy)-phosphinylmethyl] glycinate as an orange oil (7.3 grams, 46% yield), $n_D^{23}$ 1.5639.

Anal. Calculated for $C_{25}H_{28}NO_7PS$ : C, 58.02; H, 5.45; N, 2.71. Found: C, 58.22; H, 5.48; N, 2.66.

EXAMPLE 5

To a solution of methyl N-[diphenoxyphosphinylmethyl]glycinate (6.5 grams, 0.02 moles) and triethylamine (2.0 grams, 0.02 moles ) in 100 ml. of toluene at 25° C. was added 4-methylphenylsulfenyl chloride (3.1 grams, 0.02 moles) previously generated in situ to form a reaction mixture. The reaction mixture was stirred for 25 hours at a temperature of 25° C. and was then filtered forming a toluene filtrate. The resulting toluene filtrate was washed successively with cold 10% sodium hydroxide, cold water and then dried over magnesium sulfate, filtered, and concentrated on a rotary evaporator to give a clear yellow oil which crystallized on standing to give methyl N-[(4-methylphenyl)thio ]-N-[diphenoxyphosphinyl]methyl glycinate as a light yellow solid (7.2 grams, 89% ), m.p. 40°–47° C.

Calc'd. for $C_{23}H_{24}NO_5PS$: C, 60.38; H, 5.29; N, 3.06; S, 7.01. Found: C, 60.37; H, 5.32; N, 3.05; S, 7.07.

EXAMPLE 6

To a solution of ethyl N-[(bis-4-chloro-3-methylphenoxy)phosphinylmethyl]glycinate 8.2 grams, 0.018 moles) and triethylamine (1.9 grams, 0.018 moles) in 100 ml. of toluene at 0° C. was added 4-methylphenylsulfenyl chloride (2.9 grams, 0.018 moles) previously generated in situ to form a reaction mixture. The reaction mixture was allowed to warm to 25° C. and stirred for 16 hours. The reaction mixture was filtered. The resulting toluene filtrate was washed successively with cold 10% sodium hydroxide, cold water, dried over magnesium sulfate, filtered and concentrated on a rotary evaporator to give a crude product. 5.0 grams of the crude product was adsorbed onto 10 grams of oven-dried silica gel and then was extracted off by stirring in hot ethyl acetate to form an ethyl acetate mixture. The ethyl acetate mixture was filtered and concentrated to give a yellow oil which was impure by thin layer chromatography. This yellow oil was taken up in diethyl ether and washed successively again with cold 10% sodium hydroxide, cold water, dried over magnesium sulfate, filtered and concentrated to give ethyl-N-(4-methylphenylthio)-N-[bis-(4-chloro-3-methyl-phenoxy)phosphinylmethyl]glycinate as a white solid, (2.0 grams, 19% yield), m.p. 55°–58° C. An additional 3.1 grams of product could be obtained by crystallizing the remaining 5 grams of crude product from cold diethyl ether. Total yield was 5.1 grams (49% yield). Anal. Calculated for $C_{26}H_{28}Cl_2NO_5PS$: C, 54.94; H, 4.97; N, 2.46; S, 5.64. Found: C, 54.66; H, 5.00; N, 2.41; S, 5.73.

EXAMPLE 7

4-chlorophenylsulfenyl chloride (5.4 grams, 0.03 mole) was prepared in situ using the aforedescribed literature methods. The sulfenyl chloride solution was transferred under nitrogen into a cold toluene solution (100 ml) of methyl N-[(bis-2-methoxyphenoxy) phosphinylmethyl]glycinate (8.3 grams, 0.021 mole) and triethylamine (3.0 grams, 0.030 mole) to form a reaction mixture. The reaction mixture was allowed to warm to a temperature of 25° C. and stirred for 16 hours. The reaction mixture was then filtered to remove triethylamine hydrochloride. The toluene filtrate was washed with equal volumes of cold 10% aqueous sodium hydroxide and cold water, dried over magnesium sulfate and then the dried material was purified by medium pressure liquid chromatography on silica gel eluting with 60% cyclohexane, 40% ethylacetate to give methyl-N-(4-chlorophenylthio)-N-[(bis-2-methoxyphenoxy)-phosphinyl-methyl]glycinate as a yellow semi-solid (2.8 grams, 25% yield).

Anal. Calculated for $C_{24}H_{25}ClNO_7PS$: C, 53.58; H, 4.68; N, 2.60; S, 5.96. Found: C, 53.43; H, 4.72; N 2.66; S, 6.03.

EXAMPLE 8

4-methylphenylsulfenyl chloride (4.0 grams, 0.025 mole) was generated in situ using the aforedescribed literature methods. This solution was then transferred under nitrogen into a cold toluene solution (100 ml) of phenylmethyl-N-[diphenoxy)-phosphinylmethyl]-glycinate (8.6 grams, 0.021 mole) and triethylamine (2.5 grams, 0.025 mole) to form a reaction mixture. The reaction mixture was allowed to warm to a temperature of 25° C. for 2½ hours and was filtered to remove triethylamine hydrochloride. The resulting toluene filtrate was washed with equal volumes of cold 10% aqueous sodium hydroxide and cold water, dried over magnesium sulfate and then the washed material was purified by medium pressure liquid chromatography on silica gel eluting with 60% cyclohexane, 40% ethyl acetate to give phenylmethyl N-(4-methylphenylthio)-N-[diphenoxyphosphinylmethyl]glycinate as a white solid mp 108°–111° C. (1.1 grams, 10%).

Anal. Calculated for $C_{29}H_{28}NO_5PS$: C, 65.28; H, 5.29; N, 2.63; S, 6.01. Found: C, 65.31; H, 5.31; N, 2.63; S, 5.96.

EXAMPLE 9

3-Trifluoromethylphenylsulfenyl chloride (7.4 grams, 0.035 mole) was generated in situ using the aforedescribed literature methods. This solution was transferred under nitrogen into a cold toluene solution (100 ml) of methyl-N-[diphenoxy)phosphinylmethyl]glycinate (11.6 grams, 0.035 mole) and triethylamine (3.5 grams, 0.035 mole) to form a reaction mixture. The reaction mixture was allowed to warm to 25° C. slowly and stirred for 16 hours. The reaction mixture was then filtered to remove triethylamine hydrochloride. The resulting toluene filtrate was washed with equal volumes of cold 10% aqueous sodium hydroxide and cold water and dried over magnesium sulfate. The washed material was purified by medium pressure liquid chromatography on silica gel, eluting with 70% cyclohexane, 40% ethyl acetate to give methyl-N-(3-trifluoromethylphenylthio)-N-[diphenoxyphosphinylmethyl]glycinate as a light yellow oil (4.4 grams, 25% yield) $n_D^{25.6°}$ C. 1.5453.

Anal. Calculated for $C_{23}H_{21}F_3NO_5PS$: C, 54.01; H, 4.14; N, 2.74; S, 6.27. Found: C, 54.13; H, 4.20; N, 2.68; S, 6.32.

EXAMPLE 10

4-methoxy-phenylsulfenyl chloride (5.2 grams, 0.03 mole) previously prepared in situ was added to a cooled solution of methyl N-[(bis 4-methoxyphenoxy)phosphinylmethyl]glycinate (8.0 grams, 0.02 mole) and triethylamine (5.0 grams, 0.03 mole) in toluene to form a reaction mixture. The reaction mixture was stirred for 3 hours, allowing the reaction mixture to slowly warm to a temperature of 25° C. and triethylamine hydrochloride was removed by filtration. The resulting toluene filtrate was washed with cold 10% aqueous NaOH followed by cold water, dried over $MgSO_4$, filtered, and concentrated to yield 11 grams of brown oil. The brown oil was purified by medium pressure liquid chromatography on silica gel eluting with 60% cyclohexane, 40% ethyl acetate to give methyl-N-(4-methoxyphenylthio)-N-[(bis-4-methoxyphenoxy)phosphinylmethyl]glycinate as a white solid, m.p. 66°–70° C. in 52% yield.

Anal. Calculated for $C_{25}H_{28}NO_8PS$: C, 56.28; H, 5.29; N, 2.63; S, 6.01. Found: C, 56.23; H, 5.30; N, 2.63; S, 6.02.

EXAMPLE 11

2-Naphthylsulfenyl chloride (5.8 grams, 0.030 mole) was generated by adding a solution of 2-naphthalenethiol (3.7 grams, 0.03 moles) in methylene chloride to a slurry of N-chlorosuccinimide (4 grams, 0.030 mole). The reaction mixture was stirred for 2 hours, cooled in an ice bath, and carbon tetrachloride was added to precipitate all the succinimide which had formed. The mixture was then filtered under nitrogen into a solution of methyl N-[(bis-4-methoxyphenoxy)phosphinylmethyl]glycinate (7.7 grams, 0.02 moles) and triethylamine (2.1 grams, 0.02 moles) in toluene at 0° C. to form a yellow reaction mixture. The yellow reaction mixture was stirred for 16 hours and allowed to slowly warm to a temperature of 25° C. The precipitated triethylamine hydrochloride was removed by filtration. The resulting toluene filtrate was washed with cold 10% aqueous NaOH and cold water, dried over $MgSO_4$, filtered and concentrated to give a pink semi-solid. This pink semi-solid was purified by medium pressure liquid chromotography on silica gel eluting with 70% cyclohexane, 30% ethylacetate to give methyl-N-(2-naphthylthio) N-[(bis-4-methoxyphenoxy)phosphinylmethyl]glycinate as a yellow solid, m.p. 51°–54° C., in 11% yield.

Calc'd. for $C_{28}H_{28}N_1O_7P_1S_1$: C, 60.75; H, 5.10; N, 2.53; S, 579. Found: C, 60.93; H, 5.14; N, 2.70; S, 6.02.

EXAMPLE 12

The post-emergence herbicidal activity of the various compounds of this invention is demonstrated by greenhouse testing in the following manner.

A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed.

After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water.

The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

A dash in the tables indicates that the particular species of plant was absent in that test.

TABLE I

| Compound of Example No. | WAT | kg/h | A | B | C | D | E | F | G | H | I | J | K |
|---|---|---|---|---|---|---|---|---|---|---|---|---|---|
| 1 | 4 | 11.2 | 2 | 2 | 2 | 2 | 3 | 3 | 0 | 0 | 1 | 1 | 3 |
| 1 | 4 | 5.6 | 1 | 1 | 1 | 1 | 3 | 2 | 0 | 0 | 0 | 1 | 2 |
| 2 | 4 | 11.2 | 4 | 3 | 1 | 2 | 3 | 3 | 1 | 1 | 2 | 1 | 2 |
| 2 | 4 | 5.6 | 1 | 2 | 1 | 2 | 4 | 1 | 1 | 1 | 2 | 1 | 3 |
| 4 | 4 | 11.2 | 0 | 3 | 1 | 2 | 4 | 4 | 0 | 1 | 2 | 1 | 3 |
| 4 | 4 | 5.6 | 1 | 2 | 1 | 2 | 4 | 4 | 1 | 1 | 2 | 0 | 3 |
| 5 | 4 | 11.2 | 2 | 3 | 3 | 2 | 4 | 3 | 2 | 3 | 2 | 3 | 4 |
| 6 | 4 | 11.2 | — | 2 | 2 | 1 | 3 | 0 | 1 | 0 | 3 | 3 | 2 |
| 6 | 4 | 5.6 | — | 2 | 1 | 2 | 4 | 2 | 1 | 2 | 3 | 3 | 3 |
| 7 | 4 | 11.2 | 1 | 2 | 0 | 1 | 4 | 3 | 1 | 0 | 3 | 1 | 3 |
| 7 | 4 | 5.6 | 0 | 1 | 0 | 1 | 3 | 2 | 1 | 1 | 2 | 1 | 3 |
| 8 | 4 | 11.2 | 0 | 1 | 0 | 1 | 0 | 0 | 0 | 0 | 0 | 0 | 0 |
| 9 | 4 | 11.2 | 2 | 3 | 2 | 2 | 4 | 2 | 2 | 1 | 4 | 2 | 3 |
| 9 | 4 | 5.6 | 2 | 2 | 2 | 2 | 4 | 2 | 2 | 3 | 2 | 2 | 3 |
| 10 | 4 | 11.2 | 2 | 3 | 1 | 2 | 4 | 4 | 2 | 3 | 2 | 2 | 4 |
| 10 | 4 | 5.6 | 2 | 2 | 1 | 2 | 4 | 0 | 2 | 2 | 3 | 2 | 3 |
| 11 | 4 | 11.2 | 2 | 2 | 0 | 2 | 2 | 2 | 0 | 0 | 1 | 1 | 3 |

TABLE I-continued

| Compound of Example No. | WAT | kg/h | \multicolumn{11}{c}{Plant Species} |
|---|---|---|---|---|---|---|---|---|---|---|---|---|---|
| | | | A | B | C | D | E | F | G | H | I | J | K |
| 11 | 4 | 5.6 | 1 | 2 | 0 | 1 | 3 | 4 | 1 | 0 | 1 | 0 | 2 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 4 | 5.6 | 1 | 1 | 1 | 0 | 3 | 2 | 1 | 2 | 1 | 1 | 1 | 1 | 1 | 2 | 2 | 3 |
| 1 | 4 | 1.12 | 1 | 0 | 0 | 0 | 1 | 1 | 0 | 1 | 0 | 0 | 0 | 0 | 0 | 1 | 1 | 2 |
| 2 | 4 | 5.6 | 3 | 2 | 1 | 2 | 3 | 2 | 1 | 2 | 1 | 1 | 2 | 1 | 2 | 3 | 2 | 3 |
| 2 | 4 | 1.12 | 1 | 1 | 1 | 0 | 2 | 1 | 1 | 1 | 0 | 1 | 1 | 0 | 0 | 1 | 2 | 2 |
| 4 | 4 | 5.6 | 2 | 3 | 3 | 3 | 3 | 3 | 4 | 3 | 4 | — | 3 | 2 | 3 | 4 | 4 | — |
| 4 | 4 | 1.12 | 1 | 0 | 1 | 1 | 1 | 1 | 1 | 1 | — | 2 | 2 | 0 | 1 | 3 | 3 | — |
| 4 | 2 | 0.28 | 0 | 0 | 0 | 0 | 0 | 0 | 0 | 0 | 3 | 1 | 1 | 0 | 0 | 0 | 0 | — |
| 5 | 4 | 5.6 | 4 | 4 | 4 | 4 | 4 | 3 | 4 | 3 | 1 | 4 | 4 | 4 | 4 | 4 | 4 | — |
| 5 | 4 | 1.12 | 1 | 2 | 2 | 0 | 3 | 2 | 2 | 1 | 0 | 3 | 2 | 1 | 2 | 3 | 3 | — |
| 5 | 4 | 0.28 | 0 | 0 | 1 | 0 | 1 | 1 | 1 | 1 | 0 | 1 | 0 | 0 | 0 | 2 | 1 | — |
| 6 | 4 | 5.6 | 3 | 4 | 4 | 3 | 3 | 4 | 3 | 2 | 2 | 3 | 4 | 4 | 4 | 4 | 3 | — |
| 6 | 4 | 1.12 | 1 | 1 | 1 | 1 | 3 | 2 | 1 | 2 | 0 | 2 | 0 | 1 | 2 | 3 | 2 | — |
| 6 | 4 | 0.28 | 0 | 0 | 0 | 0 | 0 | 1 | 1 | 1 | 0 | 3 | 4 | 0 | 0 | 2 | 2 | — |
| 7 | 4 | 5.6 | 2 | 3 | 2 | 1 | 2 | 2 | 2 | 2 | 3 | 3 | 4 | 1 | 2 | 4 | 3 | 4 |
| 7 | 4 | 1.12 | 1 | 2 | 1 | 0 | 2 | 2 | 2 | 2 | 4 | 4 | 4 | 1 | 1 | 2 | 3 | 4 |
| 7 | 4 | 0.28 | 0 | 1 | 0 | 0 | 1 | 0 | 0 | 0 | 0 | 2 | 4 | 0 | 0 | 1 | 2 | 3 |
| 9 | 4 | 5.6 | 2 | 4 | 3 | 3 | 4 | 3 | 4 | 3 | 3 | 4 | 4 | 3 | 3 | 4 | 4 | 4 |
| 9 | 4 | 1.12 | 1 | 1 | 2 | 1 | 1 | 2 | 2 | 2 | 4 | 4 | 4 | 2 | 2 | 2 | 3 | 3 |
| 9 | 4 | 0.28 | 0 | 1 | 0 | 0 | 1 | 1 | 2 | 1 | 1 | 2 | 1 | 0 | 1 | 0 | 2 | 2 |
| 10 | 4 | 5.6 | 1 | 3 | 2 | 2 | 3 | 2 | 4 | 3 | 1 | 4 | — | 1 | 3 | 4 | 4 | 4 |
| 10 | 4 | 1.12 | 1 | 1 | 1 | 0 | 2 | 2 | 1 | 2 | 0 | 3 | — | 1 | 1 | 2 | 2 | 3 |
| 10 | 4 | 0.28 | 1 | 0 | 0 | 0 | 1 | 1 | 1 | 1 | 0 | 2 | — | 0 | 0 | 1 | 2 | 3 |
| 11 | 4 | 5.6 | 1 | 3 | 1 | 0 | 2 | 3 | 1 | 2 | 0 | 3 | — | 0 | 1 | 2 | 3 | 3 |
| 11 | 4 | 1.12 | 1 | 0 | 0 | 0 | 1 | 0 | 0 | 1 | 0 | 2 | — | 0 | 0 | 1 | 2 | 3 |
| 11 | 2 | 0.28 | 1 | 0 | 0 | 0 | 1 | 0 | 0 | 0 | 0 | 1 | — | 0 | 0 | 0 | 1 | 1 |

From the test results presented in Tables I and II, it can be seen that the post-emergent herbicidal activity of the compounds of this invention is, for the most part, general in nature. In certain specific instances, however, some selectivity is demonstrated. In this regard, it should be recognized that each individual plant species selected for the above tests is a representative member of a recognized family of plant species.

EXAMPLE 13

The pre-emergent herbicidal activity of various compounds of this invention is demonstrated as follows.

A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this example, the soil required to cover the seeds and propagules was weighed and admixed with a herbicidal composition containing a known amount of the active ingredient (compound of this invention). The pans were then filled with the admixture and leveled. Watering was carried out by permitting the soil in the pans to absorb moisture through apertures in the pan bottoms. The seed and propagule containing pans were placed on a wet sand bench and were maintained for approximately two weeks under ordinary conditions of sunlight and watering. At the end of this period, the number of emerged plants of each species were noted and were compared to an untreated control. The data is given in Tables III and IV.

The pre-emergent herbicidal activity index used below is based upon average percent control of each species as follows:

| Percent Control | Index |
|---|---|
| 0–24% control | 0 |
| 25–49% control | 1 |
| 50–74% control | 2 |
| 75–100% control | 3 |

Plant species in the tables are identified by the same code letters used in the previous example.

TABLE III

| Compound of Example No. | WAT | kg/h | A | B | C | D | E | F | G | H | I | J | K |
|---|---|---|---|---|---|---|---|---|---|---|---|---|---|
| 4 | 2 | 11.2 | 3 | 1 | 0 | 0 | 0 | 0 | 1 | 1 | 2 | 2 | 3 |
| 7 | 2 | 11.2 | 0 | 0 | 0 | 0 | 0 | 0 | 0 | 2 | 1 | 2 | 2 |
| 8 | 2 | 11.2 | 2 | 0 | 0 | 0 | 0 | 0 | 0 | 0 | 0 | 0 | 0 |
| 9 | 2 | 11.2 | 2 | 0 | 0 | 0 | 3 | 1 | 0 | 0 | 2 | 2 | 1 |
| 10 | 2 | 11.2 | 3 | 0 | 1 | 0 | 0 | — | 1 | 1 | 2 | 0 | 1 |

A dash in the tables indicates that that particular species of plant was absent in that test.

TABLE IV

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 4 | 4 | 11.2 | 1 | 0 | 0 | 0 | 1 | 1 | 0 | 0 | 0 | 0 | 0 | 0 | 0 | 2 | 1 | — |

From Tables III and IV, it can be seen that the pre-emergent herbicidal activity demonstrated some selectivity.

The herbicidal compositions, including concentrates which require dilution prior to application to the plants, of this invention generally comprise from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, for example, water, acetone, tetrahydrofuran, all parts being by weight of the total composition. Preferably, the compositions of this invention contain from 5 to 75 parts by weight of at least one compound of this invention, together with the adjuvants.

Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be employed with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some illustrative herbicidal compositions of this invention. It is to be realized that the solvents and surfactants are interchangeable in the composition.

| | |
|---|---|
| 1. Ethyl N—(2,4-dinitrophenylthio)-N—[(bis-4 methoxyphenoxy)phosphinylmethyl] glycinate as a hydrated oil | 95 parts |
| Methanol | 5 parts |
| 2. Ethyl N—(2,4-dinitrophenylthio)-N—[(bis-4 methoxyphenoxy)phosphinylmethyl] glycinate | 95 parts |
| Fumed silica | 5 parts |
| 3. Methyl N—(4-methylphenylthio)-N—[(bis-4-methoxyphenoxy)phosphinyl] glycinate | 90 parts |
| Calcium dodecylbenzene sulfonate/ ethoxylated nonyl phenol blend | 10 parts |
| 4. Methyl N—[(Diphenoxyphosphinyl)]-methyl-N—[(4-methylphenyl)thio] glycinate | 90 parts |
| Ethoxylated octyl phenol | 10 parts |
| 5. Ethyl N—(4-methylphenylthio)-N—[bis-(4-chloro-3-methylphenoxy) phosphinylmethyl]glycinate | 90 parts |
| Chloroform | 5 parts |
| Ethoxylated dinonyl phenol | 5 parts |
| 6. Methyl N—(4-chlorophenylthio)-N—[(bis-2-methoxyphenoxy)phosphinyl] glycinate | 75 parts |
| Butanol | 25 parts |
| 7. Phenylmethyl N—(4-methylphenylthio)-N—[(bis-phenoxy)phosphinyl] glycinate | 75 parts |
| Sodium dioctylsulfosuccinate | 1.25 parts |
| Calcium lignosulfonate | 2.75 parts |
| Amorphous silica (synthetic) | 21 parts |
| 8. Methyl N—(4-trifluoromethylphenylthio)-N—[(bis-phenoxy)phosphinylmethyl]glycinate | 75 parts |
| Toluene | 15 parts |
| Ethoxylated cocoamine/calcium dodecylbenzene sulfonate blend | 10 parts |
| 9. Methyl N—(4-methoxyphenylthio)-N—[(bis-4-methoxyphenoxy)phosphinylmethyl]glycinate | 45 parts |
| Methyl cellulose | 0.3 parts |
| Silica aerogel | 1.5 parts |
| Sodium lignosulfonate | 3.5 parts |
| Sodium N—methyl-N—oleyltaurate (67%) | 2.0 parts |
| Water | 47.7 parts |
| 10. Methyl N—(2-naphthylthio)-N—[(bis-4-methoxyphenoxy)phosphinylmethyl]glycinate | 50 parts |
| Dimethylformamide | 50 parts |
| 11. Ethyl N—(2,4-dinitrophenylthio)-N—[(bis-4 methoxyphenoxy)phosphinylmethyl] glycinate as a hydrated oil | 50 parts |
| Monochlorobenzene | 40 parts |
| Isopropyl dodecylbenzene sulfonate/ethoxylated castor oil blend | 10 parts |
| 12. Ethyl N—(2,4-dinitrophenylthio)-N—[(bis-4 methoxyphenoxy)phosphinylmethyl] glycinate | 50 parts |
| Dimethylsulfoxide | 40 parts |
| Ethoxylated soybeanamine | 10 parts |
| 13. Methyl N—(4-methylphenylthio)-N—[(bis-4-methoxyphenoxy)phosphinyl] glycinate | 50 parts |
| γ-butyrolactone | 25 parts |
| Ethoxylated dodecyl phenol | 25 parts |
| 14. Methyl N—[(Diphenoxyphosphinyl)]-methyl-N—[(4-methylphenyl)thio] glycinate | 50 parts |
| 1,1,1-Trichloroethane | 42 parts |
| Ethoxylated nonyl phenol | 8 parts |
| 15. Ethyl N—(4-methylphenylthio)-N—[bis-(4-chloro-3-methylphenoxy) | 25 parts |

| | | |
|---|---|---|
| phosphinylmethyl]glycinate | | |
| Chloroform | 75 | parts |
| 16. Methyl N—(4-chlorophenylthio)-N—[(bis-2-methoxyphenoxy)phosphinyl]glycinate | 25 | parts |
| Chloroform | 70 | parts |
| Ethoxylated tallow amine | 5 | parts |
| 17. Phenylmethyl N—(4-methylphenylthio)-N—[(bis-phenoxy)phosphinyl]glycinate | 10 | parts |
| Sodium lignosulfonate | 3 | parts |
| Sodium N—methyl-N—oleyltaurate (67%) | 1 | part |
| Kaolinite Clay | 86 | parts |
| 18. Methyl N—(4-trifluoromethylphenyl-thio)-N—[(bis-phenoxy)phosphinyl-methyl]glycinate | 10 | parts |
| Attapulgite granules (20–40 mesh) | 90 | parts |
| 19. Methyl N—(4-methoxyphenylthio)-N—[(bis-4-methoxyphenoxy)phosphinyl-methyl]glycinate | 10 | parts |
| Bentonite (powdered) | 90 | parts |
| 20. Methyl N—(2-naphthylthio)-N—[(bis-4-methoxyphenoxy)phosphinyl-methyl]glycinate | 10 | parts |
| Methanol | 80 | parts |
| Polyoxypropylene - polyoxyethylene block copolymer | 10 | parts |
| 21. Ethyl N—(2,4-dinitrophenylthio)-N—[(bis-4 methoxyphenoxy)phosphinylmethyl]glycinate as a hydrated oil | 10 | parts |
| Ethanol | 88 | parts |
| Polyoxyethylene (20) sorbitanmonolaurate | 2 | parts |
| 22. Ethyl N—(2,4-dinitrophenylthio)-N—[(bis-4 methoxyphenoxy)phosphinylmethyl]glycinate | 10 | parts |
| Isopropanol | 72 | parts |
| Polyoxyethylene sorbitan-monooleate | 18 | parts |
| 23. Methyl N—(4-methylphenylthio)-N—[(bis-4-methoxyphenoxy)phosphinyl]glycinate | 5 | parts |
| Dimethylformamide | 95 | parts |
| 24. Methyl N—[(Diphenoxyphosphinyl)]-methyl-N—[(4-methylphenyl)thio]glycinate | 5 | parts |
| Acetonitrile | 90 | parts |
| Ethoxylated tallow amine | 5 | parts |
| 25. Ethyl N—(4-methylphenylthio)-N—[bis-(4-chloro-3-methylphenoxy)phosphinylmethyl]glycinate | 5 | parts |
| Ethanol | 94 | parts |
| Ethoxylated tallow amine | 1 | part |
| 26. Methyl N—(4-chlorophenylthio)-N—[(bis-2-methoxyphenoxy)phosphinyl]glycinate | 5 | parts |
| Isopropanol | 80 | parts |
| Ethoxylated cocoamine | 15 | parts |

Several compounds of this invention are useful as plant growth regulators as hereafter described in Example 14.

EXAMPLE 14

In determining the regulatory effects of the compounds of this invention on sugarcane, it should be noted that the appropriate rate of application can vary from about 0.12 kg/hectare to about 5.6 kg/hectare.

Depending upon local cultural practices in various areas around the world, sugarcane is grown for from about 9 to about 30 months before harvest, and it is thus necessary to consider both the chronological age and the maturity stage of the cane in rate determinations. Application of the treatment to the sugarcane is generally made from about 2 to 12 weeks prior to the scheduled harvest date. Preferably, such applications are made from 3 to 10 weeks before said date.

In this example individual sugarcane stalks were treated with compounds of this invention 4 and 5 weeks before harvest. To avoid sampling errors, older cane, preferably from about 13 to about 23 months old, was employed in the tests. For each compound employed, at least 5 stalks were employed, processed and the total values of pol percent cane and juice purity obtained were for each stalk. An identical number of untreated sugarcane stalks of the same age were similarly processed to provide a control. A comparison of the values obtained for the treated cane with corresponding values of the control sample provided a convenient means of determining the regulatory effectiveness of these compounds which is hereafter shown in Table IV.

The analyses were carried out by the press method developed by T. Tanimoto and reported in Hawaiian Planters' Record, Volume 57, pp. 133–150 (1964). The data are expressed as Juice Purity and Pol Percent Cane. Pol Percent Cane is defined as a polarimetric determination and equals the percentage of sucrose if it is the only substance in the solution which will rotate the plane of polarized light. A determination of Pol Percent Cane is considered by those skilled in the art as an effective means of determining the sucrose content of sugarcane juice.

In order to convert a change in Pol Percent Cane into a corresponding change in the quantity of sugar obtained, it is first necessary to know the average normal yield of sugar in the area under test. Here, the tests are carried out in a region where about 225 to 245 metric tons of cane are harvested per hectare, and about 22.5 metric tons of sugar are obtained from this quantity of cane. With this average normal yield of 22.5 metric tons per hectare, an increase of just 0.1 Pol Percent Cane translates to an increase of about 225 kg of sugar per hectare.

In this example, about 38 mg. of a compound of this invention was dissolved in about 0.3 ml. of water. This solution was then applied to the whorl of each of the sugarcane stalks to be tested with the exception of the control stalks. At the time of application, internode number 13 on each stalk was marked as a reference point. At 4 and 5 weeks after treatment (WAT), the sugarcane plants were harvested, and the portion from the reference point to the shoot apex of each stalk of a treated or untreated group was removed, combined and analyzed as described. The results obtained were shown in Table IV.

TABLE IV

| | 4 WAT | | 5 WAT | |
|---|---|---|---|---|
| | Juice Purity | Pol % Cane | Juice Purity | Pol % Cane |
| Treated Compound (A) | 73.52 | 8.20 | 74.29 | 8.01 |
| Untreated | 62.36 | 5.58 | 67.06 | 6.27 |
| Treated Compound (B) | 83.15 | 11.92 | 84.29 | 12.39 |
| Untreated | 79.55 | 10.05 | 81.90 | 10.92 |

Wherein compound (A) is ethyl-N—(2,4 dinitrophenylthio-N—[(bis-4-methoxy)-phenoxyphosphinylmethyl]glycinate of Example 2.
Wherein compound (B) is methyl-[N—(4-methyl-phenylthio)-N—methoxyphenoxy)phosphinyl]glycinate of Example 4.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters including conventional tractor mounted sprayers, portable knapsack sprayers, portable powdered sprayers and mist blowers. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another application method, shielded applicators may be employed to direct the liquid composition in the form of a spray onto the weeds while effectively shielding the crops from the spray.

These and other application methods for selectively applying liquid compositions to weeds are discussed in detail in Innovative Methods of Post-Emergence Weed Control, McWhorter C.G., Southern Weed Science Society, 33rd Annual Meeting Proceedings, Jan. 15–17, 1980; Auburn University Printing Service, Auburn, Ala. U.S.A., the teachings of which are incorporated herein by reference in their entirety.

Another method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

The aforementioned and other methods for applying liquid compositions to plants are discussed in detail in "Rope Wick Applicator-Tool With A Future", Dale, James. E., pp. 3–4, "The Recirculating Sprayer and Roundup ® Herbicide", Derting, Claude W., pp. 5–7, and "C.D.A. Herbicide Application", McGarvey, Frank X., Weeds Today, Volume 11, Number 2, pp. 8–9, Late Spring, 1980, 309 W. Clark St., Champaign, Ill., the teachings of which are incorporated herein by reference in their entirety.

Other application methods include the electrodyn spray system wherein the spray stem atomizes and propels electrically charged droplets along the thin lines in an electrical field set up between a high voltage positively charged nozzle, the nozzles themselves, and the earth's target crop. The aforedescribed spray system is discussed in detail in Ag. Chem. Dealer/Applicator, Aug. 1980, pp. 29–30, British Pat. No. 1,569,707 and British Patent Application No. 2,022,418. The teachings of these articles are incorporated herein in their entirety by reference.

Systems employing vertically disposed rollers may be employed such as those disclosed in FIG. 9 of La Sacrerie Belge, June 1976, Vol. 95, p. 224.

Additionally, another spray system comprises a box like structure which encloses an undesired plant. When the undesired plant is sprayed via nozzles, the spray cannot drift into adjacent plants which are outside the box. The unused liquid composition is collected for re-use with a pipe. The aforementioned apparatus and technique is discussed in detail in La Sacrerie Belge, Vol. 95, June 1976, pp. 222–223 and Le Betteravier No. 778, July/August 1974, p. 10. The teachings of these articles are incorporated herein in their entirety by reference.

Applicators may be of the magic wand type as described in British Pat. No. 1,303,967 or of the glove type as described in British Pat. No. 1,282,002. These applicators are discussed in British Pat. Nos. 1,508,709 and 1,535,095 and British Patent Application No. 2,004,724, wherein rotatable elements such as rotatable drums covered with suitable absorbent are employed.

Those of skill in the art will recognize that the physical properties such as the particular size of any slurried or dissolved components of the aforementioned formulations will influence the selection of the particular method for applying formulations to emerged plants as will the intended use of the compounds of this invention.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

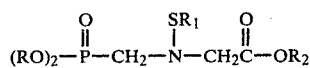

wherein R is phenyl, naphthyl, biphenylyl, benzyl or naphthyl, biphenylyl, benzyl or phenyl substituted with from one or two substituents independently selected from the group consisting of hydrogen, lower alkyl, lower alkoxy, lower alkylthio, trifluoromethyl, alkoxycarbonyl, methylenedioxy, cyano, nitro and halogen; $R_1$ is phenyl, naphthyl or phenyl substituted with from one or two substituents independently selected from the group consisting of hydrogen, lower alkyl, lower alkoxy, halogen, trifluoromethyl and nitro; and $R_2$ is selected from the group consisting of lower alkyl and lower aralkyl.

2. A compound according to claim 1 wherein R is phenyl or substituted phenyl.

3. A compound according to claim 2 wherein $R_1$ is phenyl substituted with from one or two substituents independently selected from the group consisting of hydrogen, lower alkyl, nitro, lower alkoxy, halogen and trifluoromethyl.

4. A compound according to claim 3 wherein said compound is ethyl N-(2,4-dinitrophenylthio)-N-[(bis-4-methoxyphenoxy)phosphinylmethyl]glycinate.

5. A compound according to claim 2 wherein said compound is methyl N-(4-methylphenylthio)-N-[(bis-4-methoxyphenoxy)phosphinyl]glycinate.

6. A compound according to claim 3 wherein said compound is methyl N-[(4-methylphenyl)thio]-N-diphenoxyphosphinylmethylglycinate.

7. A compound according to claim 3 wherein said compound is ethyl N-(4-methylphenylthio)-N-[bis(4-chloro-3-methylphenoxy)phosphinylmethyl]glycinate.

8. A compound according to claim 2 wherein said compound is methyl N-(4-chlorophenylthio)-N-[(bis-2-methoxyphenoxy)phosphinylmethyl]glycinate.

9. A compound according to claim 3 wherein said compound is phenylmethyl N-(4-methylphenylthio)-N-[diphenoxyphosphinylmethyl]glycinate.

10. A compound according to claim 3 wherein said compound is methyl N-(3-trifluoromethylphenylthio)-N-[diphenoxyphosphinylmethyl]glycinate.

11. A compound according to claim 2 wherein said compound is methyl N-(4-methoxyphenylthio)-N-[(bis-4-methoxyphenoxy)phosphinylmethyl]glycinate.

12. A compound according to claim 2 wherein said compound is methyl N-(2-naphthylthio)-N-[(bis-4-methoxyphenoxy)phosphinylmethyl]glycinate.

* * * * *